United States Patent [19]

Imaizumi et al.

[11] Patent Number: 5,334,593
[45] Date of Patent: Aug. 2, 1994

[54] ANXIOLYTIC DRUGS

[75] Inventors: Masahiro Imaizumi; Shinji Sakata, both of Choshi, Japan

[73] Assignee: Yamasa Shoyu Kabushiki Kaisha, Chiba, Japan

[21] Appl. No.: 867,712

[22] PCT Filed: Jan. 11, 1991

[86] PCT No.: PCT/JP91/00015
§ 371 Date: Jul. 9, 1992
§ 102(e) Date: Jul. 9, 1992

[87] PCT Pub. No.: WO91/10432
PCT Pub. Date: Jul. 25, 1991

[30] Foreign Application Priority Data

Jan. 13, 1990 [JP] Japan .................................. 2-4728

[51] Int. Cl.$^5$ ............................................ A61K 31/505
[52] U.S. Cl. ................................................ 514/274
[58] Field of Search ................................... 514/274

[56] References Cited

FOREIGN PATENT DOCUMENTS

WO9001027 8/1990 Japan .

OTHER PUBLICATIONS

Japanese Abstract: JP-A-57-042624 (Mar. 10, 1982) "Antianxiety Agent with Antidepressant Activity".
Japanese Abstract: JP-A-207218 (Sept. 11, 1987) "Central Nervous System Depressant".
JP 62-93281 (A), Kyowo Hakko Kogyo Co., Ltd. Japan, Apr. 28, 1987, (abstract).

Primary Examiner—Frederick E. Waddell
Assistant Examiner—M. Moezie
Attorney, Agent, or Firm—Wenderoth, Lind & Ponack

[57] ABSTRACT

The present invention relates to an anxiolytic drug comprising as an active ingredient a 1-amino-5-halogenouracil represented by formula [I]:

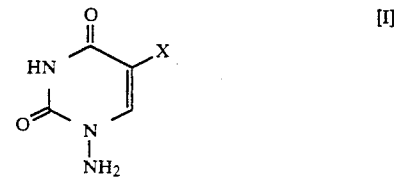

wherein X represents a halogen atom, or pharmaceutically acceptable salt thereof.

2 Claims, 5 Drawing Sheets

ANXIOLYTIC DRUGS

TECHNICAL FIELD

The present invention relates to anxiolytic drugs containing a 1-amino-5-halogenouracil as an active ingredient.

BACKGROUND ART

An anxiolytic drug (minor tranquilizer) is a therapeutic agent which is effective in treating anxiety and which can eliminate anxiety or psychentonia in a dose that will not induce excessive sedation. A typical therapeutic agent which is presently used as an anxiolytic drug is a benzodiazepine-type anxiolytic.

Heretofore, (1) bromacil (see Japanese Patent Laid-Open Publication No. 42624/1982), and (2) $N^3$-substituted (e.g., benzyl-substituted) uridine derivatives (see Japanese Patent Laid-Open Publication No. 207218/1987) have been known as uracil derivatives having anxiolytic activity or being expected to have the same.

We previously found that 1-amino-5-halogenouracil has sedative effects on central nervous system, and filed therefore an application for a patent (PCT/JP89/00708). As a 1-amino-5-halogenouracil, 1-amino-5-fluorouracil is so far known. However, it has not yet been reported that the compound has anxiolytic activity (see Sci. Pharm., 52, 46 (1984); and Japanese Patent Laid-Open Publication No. 93281/1987).

Benzodiazepine-type anxiolytic drugs which are now widely used as anxiolytic drugs, typically diazepam, give rise to various side effects (e.g., muscle relaxation, sedation, and elicitation of amnesia). The use of the anxiolytic drugs of this type therefore brings about clinical problems. Since the above side effects are common to compounds having a benzodiazepine skeleton, there exists a demand for finding out a compound which has a skeleton other than the benzodiazepine and which can be used as an anxiolytic drug.

Further, among the above-described uracil derivatives having anxiolytic activity, the bromacil referenced as (1) exhibits low anxiolytic activity when it is orally administered, and the minimum effective dose thereof for single administration is as high as 100 mg/kg. Therefore, the expected effects cannot be fully obtained unless a large amount of the bromacil is administered. With respect to the $N^3$-substituted uridine derivatives referenced as (2), although the aforementioned patent publication discloses their hypnotic effects, their anxiolytic activity and particular data regarding the same are not disclosed therein.

An object of the present invention is to provide an anxiolytic drug which comprises as an active ingredient a compound which has a uracil skeleton and low side effects such as those mentioned above.

DISCLOSURE OF THE INVENTION

We have conducted extensive research in order to find out a compound which has anxiolytic activity. As a result, we have found that 1-amino-5-halogenouracil has excellent anxiolytic activity.

The present invention therefore provides an anxiolytic drug (hereinafter often referred to simply as "the drug of the present invention") which comprises as an active ingredient a 1-amino-5-halogenouracil represented by formula [I]:

wherein X represents a halogen atom, or a pharmaceutically acceptable salt thereof.

The present invention also provides a method of treating anxiety in mammal, which comprises administering an effective dose of a compound represented by the above formula [I] or a pharmaceutically acceptable salt thereof to a mammal in a state of anxiety.

Furthermore, the present invention provides the use of a compound represented by the above formula [I] or a pharmaceutically acceptable salt thereof for the manufacture of an anxiolytic drug.

As is apparent from the results of Test Example 1 which will be described later, the compound having the above formula [I] or its pharmaceutically acceptable salt (hereinafter often referred to as "the compound of the present invention"), which is an active ingredient of the drug of the present invention, shows potent anti-conflict activity comparable to that of diazepam when it is orally administered in a dose of 50 mg/kg or less. Moreover, when the compound of the present invention is administered, the decrease in the number of lever pressing during the safety periods is smaller than that when diazepam is administered. For this reason, it is presumed that the compound of the present invention does not practically cause serious side effects such as sedative activity which result in clinical problems. Further, with respect to the compound of the present invention, the results of Test Example 3, which will also be described later, clearly demonstrate that the difference between the dose at which muscle relaxation, which is one of the side effects, is induced and the dose at which anxiolytic activity is considered to be enough as an anxiolytic drug is large. It can thus be said that the compound of the present invention provides a therapeutic agent having high validity. Furthermore, it is evident from the results of the later-described Test Examples 4 and 5 that the compound of the present invention shows low toxicity when tested with mice. The compound of the present invention has thus proved to provide a therapeutic agent which is highly safe. For these reasons, a therapeutic agent comprising the compound of the present invention as an active ingredient is useful as an anxiolytic drug.

BRIEF DESCRIPTION OF THE DRAWINGS

FIG. 1 consists of three graphs respectively showing the relationship between the number of lever pressing during the alarm periods and the time elapsed, obtained in Test Example 1 in which 1-amino-5-chlorouracil (FIG. 1A), 1-amino-5-bromouracil (FIG. 1B) or 1-amino-5-fluorouracil (FIG. 1C) was administered. The time elapsed (minutes) after the administration of the test compound is plotted in abscissa, and the cumulative number of lever pressing only during the alarm periods is plotted in ordinate. FIG. 2 consists of two graphs respectively showing the change in the number of lever pressing at each dose of the test compound, in which, immediately after the administration of the test compound, the number was counted over a period of one hour and the change was expressed by % increasing relative to control (FIG. 2A: safety periods; FIG. 2B: alarm periods).

In the figures, ACU denotes a group of mice to which 1-amino-5-chlorouracil was administered, ABU denotes a group of mice to which 1-amino-5-bromouracil was administered, AFU denotes a group of mice to which 1-amino-5-fluorouracil was administered, and DZP denotes a group of mice to which diazepam was administered.

BEST MODE FOR CARRYING OUT THE INVENTION

The active ingredient of the drug of the present invention is a 1-amino-5-halogenouracil represented by the above formula [I] or a pharmaceutically acceptable salt thereof.

Fluorine, iodine, bromine or chlorine is exemplified as a halogen atom represented by X in the formula [I].

The compound of the present invention may also be in the form of a pharmaceutically acceptable salt when used as the drug of the present invention. Examples of such salts include acid addition salts with inorganic acids such as hydrochloric acid, hydrobromic acid, sulfuric acid and phosphoric acid, or with organic acids such as citric acid, acetic acid, succinic acid, maleic acid, methanesulfonic acid and p-toluenesulfonic acid.

The compound of the present invention can be prepared, for example, by the method in which a pyrimidine derivative represented by the following formula [A] is used as a starting compound, which is reacted with an aminating agent (Z-NH$_2$) to obtain an intermediate [B] by the specific amination of the 1-position of the pyrimidine derivative (referred to hereinafter as "amination reaction"), and the protective groups represented by R are removed (referred to hereinafter as "deprotection reaction"):

wherein X has the same meanings as defined above, R represents a protective group and Z—NH$_2$ represents an aminating agent.

The halogen atom represented by X in the starting compound [A] may be selected appropriately so that it corresponds to X in the desired compound of the present invention. The protective groups represented by R include silyl groups such as trimethylsilyl, triethylsilyl, t-butyldimethylsilyl, methyldiisopropylsilyl and triisopropylsilyl, and alkyl groups such as methyl and ethyl. Particularly, the silyl groups are advantageously used.

The starting compound [A] can be prepared by introducing the protective groups represented by R into a 5-halogenouracil according to a conventional method. For example, when a silyl group is used as the protective group, the starting compound [A] can be prepared by using 2- to 10-fold moles of the silylating agent in proportion to 1 mole of the 5-halogenouracil and reacting the mixture in a reaction solvent such as pyridine, picoline, diethylaniline, dimethylaminopyridine, dimethylformamide, acetonitrile, tributylamine, triethylamine or the like, which may be used alone or in admixture thereof, at a reaction temperature in the range of 0° to 50° C. for 1 to 30 hours.

After introducing the protective groups, the pyrimidine derivative represented by the above formula [A] is isolated and purified, if necessary, by a conventional isolation and purification means for nucleic acid bases such as distillation, adsorption chromatography with silica gel or the like, or recrystallization, and then subjected to amination reaction as the starting compound.

The aminating agent (Z—NH$_2$) used for the amination reaction includes o-arylsulfonylhydroxylamines and o-nitrophenylhydroxylamines. Specifically, there can be mentioned, as o-arylsulfonylhydroxylamines, o-mesitylenesulfonylhydroxylamine, o-(2,4,6-triisopropylbenzenesulfonyl)hydroxylamine, o-(2-nitrobenzenesulfonyl)hydroxylamine and the like, and, as o-nitrophenylhydroxylamines, o-(2,4-dinitrophenyl)hydroxylamine, o-picrylhydroxylamine and the like.

The amination reaction with these aminating agents can be accomplished by using 1- to 5-fold moles of an aminating agent, preferably 1- to 1.5-fold moles in proportion to 1 mole of the starting compound [A] and reacting the mixture in a reaction solvent (a halogenated hydrocarbon such as dichloromethane, dichloroethane, or chloroform, an ether type solvent such as tetrahydrofuran, or dioxane, or an aromatic hydrocarbon such as benzene, toluene, or xylene, which may be used alone or in admixture thereof) at a reaction temperature in the range of 0° to 50° C., preferably 0° to 30° C. for 1 to 10 hours.

After the amination reaction, the intermediate is subjected to deprotection reaction to obtain the compound of the present invention.

The deprotection reaction may be conducted according to any conventional method for the deprotection of the protective group used. For example, when a silyl group is used as the protective group, it can be removed by ammonium fluoride treatment or acidic or alkaline hydrolysis. Also, when an alkyl group such as methyl or ethyl is used, the alkyl group can be removed by acidic or alkaline hydrolysis.

The compound of the present invention thus obtained can be isolated and purified by an appropriate combination of conventional isolation and purification means, for example, chromatography such as adsorption chromatography or recrystallization which are applied to the isolation and purification of nucleic acid bases. Further, the compound of the present invention in the form of acid addition salt can be prepared by a conventional method using an inorganic or organic acid as described above and selected depending on the type of the desired salt.

While the dose of the compound of the present invention represented by the formula [I] as the active ingredient of the drug of the present invention depends on many factors such as the severity of the patient and the acceptability of the drug and finally should be determined by the judgement of the doctor, it is generally in the range of 0.001 to 2 g per day for an adult patient, which is administered once or in portions. The route for administration of the drug may be any of the appropriate routes such as oral or parenteral administration.

The drug of the present invention can be formulated as a preparation suitable for the intended administration route thereof. Such preparation can be prepared, according to a conventional method, with the addition of a pharmaceutically acceptable carrier or adjuvant to the compound of the present invention.

For oral administration, the drug may be in the form of a solid preparation such as powder, granules, capsules or tablets or a liquid preparation such as syrup or elixir. For parenteral administration, the drug may be in the form of injection, suppository, agent for external application or for inhalation. It is also possible to formulate the drug as a sustained release preparation by a well-known technique.

In the production of the solid preparation for oral administration, the compound of the present invention is mixed with an excipient such as lactose, starch, crystalline cellulose, calcium lactate, calcium monohydrogenphosphate, magnesium aluminometasilicate or anhydrous silicic acid to obtain a powder, or, if necessary, the powder is further mixed with a binding agent such as refined sugar, hydroxypropylcellulose or polyvinylpyrrolidone, or a disintegrating agent such as carboxymethylcellulose or carboxymethylcellulose calcium for wet or dry granulation to obtain granules. In the production of tablets, these powders or granules, if necessary, mixed with a lubricant such as potassium stearate, magnesium stearate or talc may be punched into tablets. Alternatively, these granules or tablets can be coated with an enteric base such as hydroxypropylmethylcellulose phthalate or a methyl methacrylate copolymer to obtain enteric-coated preparations, or they can be coated with ethylcellulose, carnauba wax or a hydrogenated oil to obtain sustained release preparations. Further, in order to prepare capsules, powder or granules may be charged into hard capsules, or the compound of the present invention is first dissolved in glycerol, polyethylene glycol, sesame oil, olive oil or the like and next coated with a gelatin film to obtain soft capsules.

In order to prepare the liquid preparation for oral administration, the compound of the present invention and a sweetener such as refined sugar, sorbitol or glycerol may be dissolved in water to obtain a clear syrup, or the syrup may be further mixed with an essential oil or ethanol to obtain an elixir or with gum arabic, tragacanth gum, polysorbate 80, or carboxymethylcellulose sodium to obtain an emulsion or a suspension. These liquid preparations may also contain flavoring agents, colorants, preservatives or the like, if desired.

In order to prepare the preparation for injection, the compound of the present invention may be dissolved in distilled water for injection, if necessary, together with a pH adjusting agent such as sodium hydroxide, hydrochloric acid, lactic acid, sodium lactate, sodium monohydrogenphosphate or sodium dihydrogenphosphate, and an isotonizing agent such as sodium chloride or glucose, aseptically filtered and charged into ampoules, or these solutions may be mixed with mannitol, dextrin, cyclodextrin, or gelatin and lyophilized under vacuum to obtain injections which should be dissolved on use. Furthermore, the compound of the present invention can be mixed with lecithin, polysorbate 80, or polyoxyethylenehydrogenated castor oil, and the mixture is emulsified in water to obtain an emulsion for injection.

In order to prepare the preparation for rectal administration, the compound of the present invention may be melted by heating together with a suppository base such as tri-, di- or mono-glycerides of cacao fatty acid or polyethylene glycol, poured into a mold and cooled, or the compound of the present invention may be dissolved into polyethylene glycol or soybean oil and coated with a gelatin film.

In order to prepare the preparation for external application, the compound of the present invention is added to white vaseline, beeswax, liquid paraffin or polyethylene glycol and the mixture is kneaded, if necessary, under heat to obtain an ointment, or it is kneaded with an adhesive such as rosin or an alkyl acrylate polymer and then spread over nonwoven fabrics made of, for example, polyethylene to obtain a tape preparation.

EXAMPLES

The present invention will be specifically illustrated below with reference to Synthesis Examples, Test Examples and Preparation Examples.

Synthesis Example 1

1-Amino-5--fluorouracil

5-Fluorouracil was silylated as usual with hexamethyldisilazane, and then 8.8 g (32 mmole) of 2,4-ditrimethylsilyloxy-5-fluoropyrimidine thus obtained, distilled and purified was dissolved in dichloromethane (48 ml). To the solution was added 7.5 g (35 mmole) of o-mesitylenesulfonylhydroxylamine (MSH) under ice-cooling, and the mixture was reacted with stirring at room temperature for 4 hours.

After reaction, the reaction solution was concentrated under reduced pressure. Distilled water (200 ml) was added to the residue, and oily impurities were extracted with chloroform (50 ml) from the mixture. The aqueous phase was neutralized with a weakly basic resin and then concentrated to dryness under reduced pressure.

The crude crystal thus obtained was purified by sublimation at 150° C. and 5 mmHg to obtain 2.9 g (yield, 62%) of 1-amino-5-fluorouracil.

The product was further recrystallized from 50% ethanol to obtain colorless needle crystals. M.P.: 196°–199° C. (lit. 205°–207° C.)

Elementary analysis for $C_4H_4N_3O_2F$:
Calculated (%): C, 33.11; H, 2.78; N, 28.96;
Found (%): C, 33.15; H, 2.79; N, 28.78.

Synthesis Example 2

1-Amino--5--bromouracil

After the silylation of 5-bromouracil conducted in the same manner as in Synthesis Example 1, 8.8 g (26 mmole) of 5-bromo-2,4--ditrimethylsilyloxypyrimidine distilled and purified was dissolved in 50 ml of dichloromethane. To the solution was added 6.7 g (31 mmole) of MSH under ice-cooling, and the mixture was reacted with stirring at room temperature for 4 hours.

After reaction, the reaction solution was concentrated under reduced pressure. To the residue were added distilled water (200 ml) and subsequently 2N- sodium hydroxide to adjust the pH to 6.0, and the solution was concentrated under reduced pressure.

The crude product thus obtained was collected by filtration and recrystallized from 50% ethanol to obtain 3 g (yield, 55%) of crystalline 1-amino-5--bromouracil. M.P.: 214°–215° C.

Elementary analysis for $C_4H_4N_3O_2Br$:
Calculated (%): C, 23.32; H, 1.96; N, 20.40;
Found (%): C, 23.59; H, 1.97; N, 20.14.
$^1$H-NMR spectrum ($\delta$, ppm, DMSO--$d_6$):
5.54 (2H, s, $NH_2$, disappeared by the addition of $D_2O$)
8,14 (1H, s, 6-H)
11.84 (1H, s, NH, disappeared by the addition of $D_2O$)

Synthesis Example 3

1-Amino--5--chlorouracil

Starting from 5-chlorouracil, 1-amino-5-chlorouracil was obtained in the same manner as in Synthesis Example 2. M.P.: 224°–225° C. (recrystallized from water)
Elementary analysis for $C_4H_4N_3O_2Cl$:
Calculated (%): C, 29.74; H, 2.50; N, 26.01;
Found (%): C, 29.83; H, 2.55; N, 25.93.
$^1$H-NMR spectrum ($\delta$, ppm, DMSO--$d_6$):
5.54 (2H, s, $NH_2$, disappeared by the addition of $D_2O$)
8.09 (1H, S, 6-H)
11.86 (1H, S, disappeared by the addition of $D_2O$)

Synthesis Example 4

1-Amino--5--iodouracil

Starting from 5-iodouracil, 1-amino-5-iodouracil was obtained in the same manner as in Synthesis Example 2. M.P.: 195°–196° C. (recrystallized from water)
Elementary analysis for $C_4H_4N_3O_2I$:
Calculated (%): C, 18.99; H, 1.59; N, 16.61;
Found (%): C, 19.05; H, 1.57; N, 16.51.
$^1$H-NMR spectrum ($\delta$, ppm, DMSO-$d_6$):
5.51 (2H, s, $NH_2$, disappeared by the addition of $D_2O$)
8.08 (1H, s, 6-H)
11.69 (1H, s, disappeared by the addition of $D_2O$)

Test Example 1

Anti-Conflict Activity.(Geller Type)

The activities of the test compounds were evaluated by the Geller type conflict test which is frequently employed as a preclinical evaluation method of an anxiolytic drug [see Psychophamacologia, 1, 482–492 (1960)]. The method is described below.

1-Amino--5--chlorouracil (ACU), 1-amino-5-bromouracil (ABU) and 1-amino-5-fluorouracil (AFU) were used as the test compounds. These compounds were respectively suspended in distilled water containing 0.5% carboxymethyl cellulose (CMC) to obtain suspensions suitable for oral administration. In addition, diazepam (DZP) serving as a positive control compound was also prepared as a suspension suitable for oral administration in the same manner.

A skinner box (manufactured by OHARA & Co., Ltd.) used for the test was equipped with a lever, a light and a buzzer, and its floor was a grid made of stainless steel. When the lever was pressed, pellets (food) were supplied from a feeder, and, if necessary, an electric shock was given from the floor.

Male Wistar rats were deprived of food during the night to restrain an increase in the body weight, and a training of the animals was started. After the number of lever pressing performed by the rats reached the predetermined level by following a reinforcement schedule in which food pellets were supplied once every ten times of lever pressing (FR-10), two periods, that is, a 7-minute safety period and a 3-minute alarm period were alternately incorporated in the schedule - During the alarm period, the rats were signaled by the light and buzzer, and further by an electric shock given from the floor every time they were supplied with food pellets. Those rats which were trained to press the lever 19 times or less during the alarm period were used for the measurement. Immediately after a suspension of a test compound prepared in the above-described manner was administered orally to the rats, they were placed in the skinner box, and the numbers of lever pressing were counted over a period of one hour. The numbers thus obtained were compared with those obtained by the control wherein distilled water containing 0.5% CMC and no test compound was orally administered to the rats and the number of lever pressing was counted for one hour. The significant difference was ascertained by the Wilcoxoh's signed rank test. The results are shown in FIG. 1A, FIG. 1B, FIG. 1C, FIG. 2A and FIG. 2B.

To the rats used for the above test, no drugs were administered for one week, and then they were repeatedly used for the same test.

As is evident from the results shown in the figures, the ACU, at the doses of 20 and 30 mg/kg, significantly increased the number of lever pressing during the alarm periods, while it did not significantly change the number of lever pressing during the safety periods; the ABU, at the doses of 10, 30 and 50 mg/kg, significantly increased the number of lever pressing during the alarm periods, while it did not significantly change the number of lever pressing during the safety periods; and the AFU, at the dose of 20 mg/kg, significantly increased the number of lever pressing during the alarm periods, while it did not significantly change the number of lever pressing during the safety periods. It is noted that the DZP which was used as a positive control compound, at the doses of 5, 10 and 20 mg/kg, significantly increased the number of lever pressing during the alarm periods, but significantly decreased the number of lever pressing during the safety periods at the doses of 20 and 50 mg/kg.

Test Example 2

Anti-Conflict Activity (Vogel Type)

By using a test box for mice (manufactured by OHARA & Co., Ltd.), the anti-conflict activity of a test compound was determined by the Vogel type conflict test [see Psychopharmacologia (Berl.), 21, 1–7 (1971)]. The method is described below.

Male ICR mice (6 weeks old) were deprived of water for one day before the test. The mice were then individually placed in the test box, and given water ad libitum for 10 minutes. Thereafter, they were placed back in their home cages, given water ad libitum overnight, and again deprived of water for two days. The mice thus treated were used for the measurement.

ABU, the test compound, was suspended in physiological saline containing 0.5% CMC, and the suspension was administered intraperitoneally to the above mice. On the other hand, as a positive control compound, DZP was administered in the same manner. Fifteen minutes after the administration, the mice were placed in the test box, and allowed to freely drink one count of water (one drop: approximately 40 ul ). Thereafter, a 50 V electric foot shock was given from the grid floor to the mice every time they drunk one count of water. Under such conditions, the number of water-drinking was counted over a period of 10 minutes. The number of water-drinking performed by a group of mice to which the test compound was administered was compared with that of water-drinking performed by a group of mice to which a vehicle (physiological saline containing 0.5% CMC and no test compound) was administered.

The significant difference was ascertained by the Mann-Whitney's U-test. The results are shown in FIG. 3.

Figure 1A:
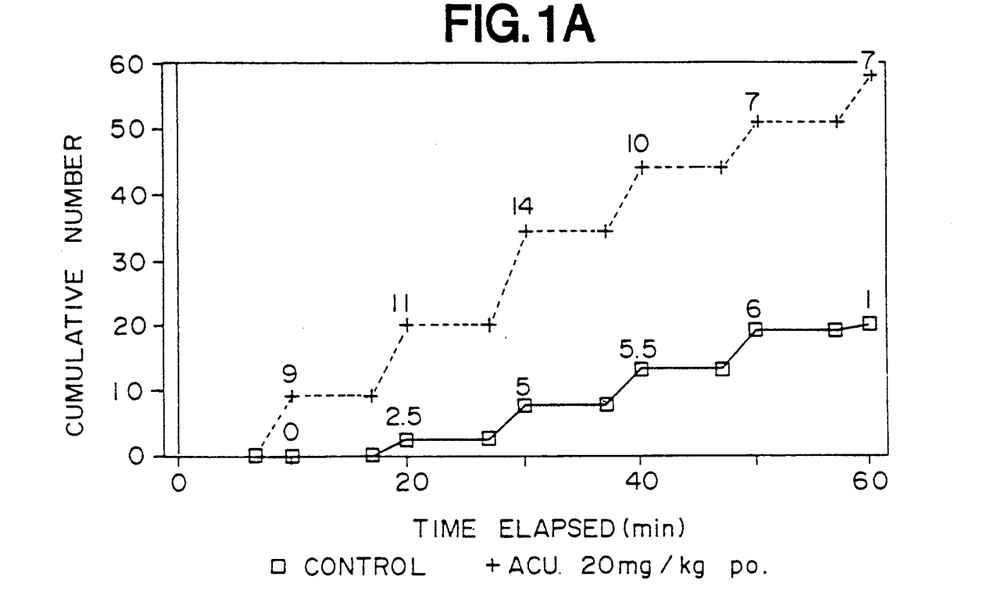
Figure 1B:
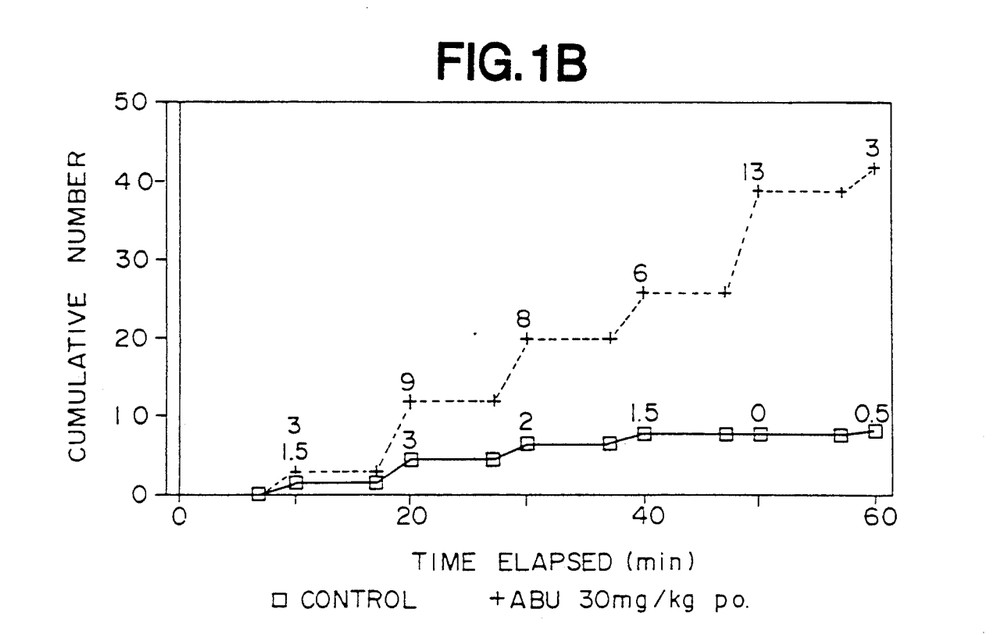
Figure 1C:
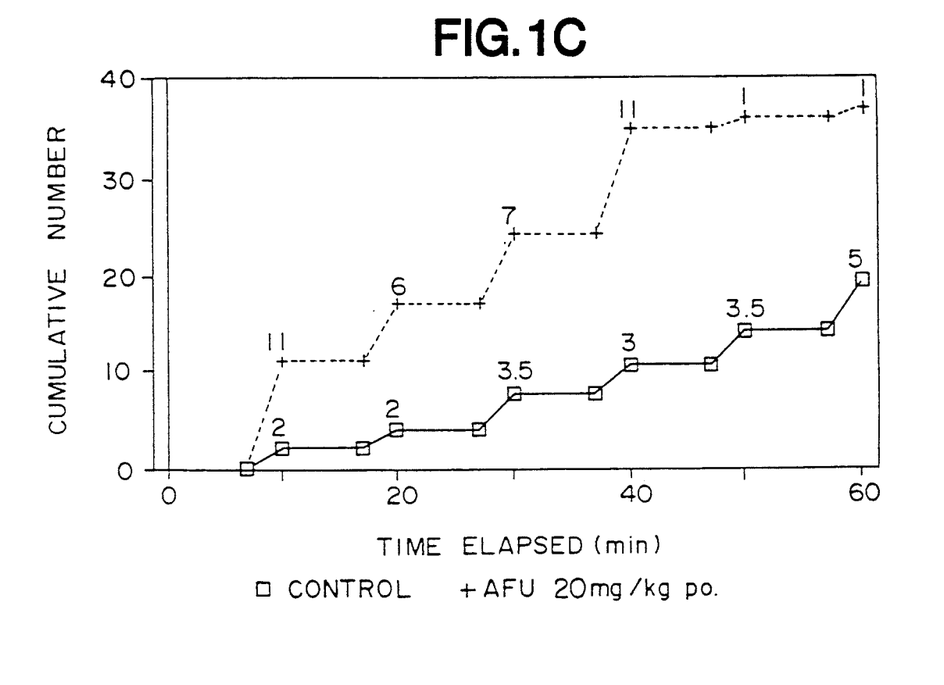
Figure 2A:
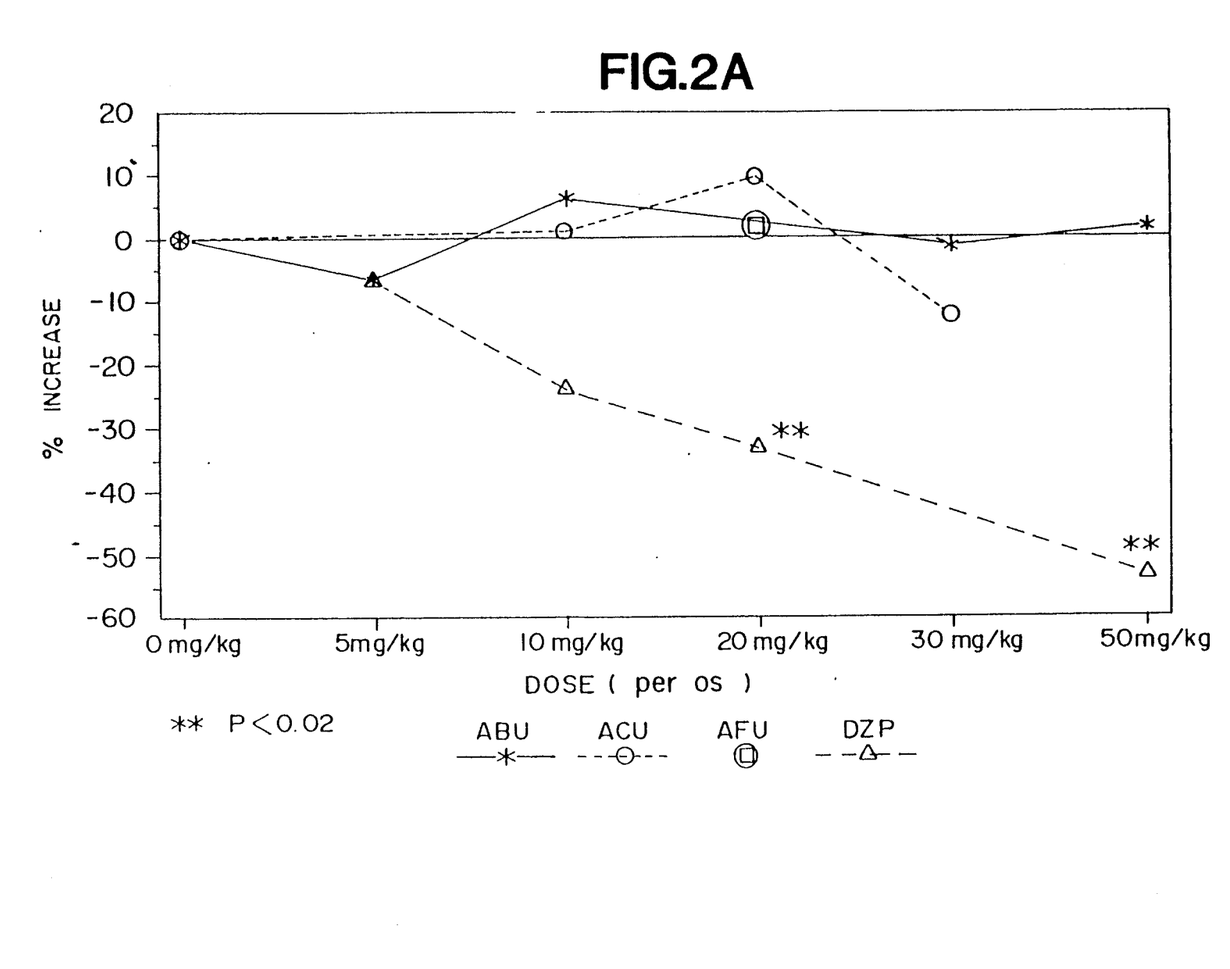
Figure 2B:
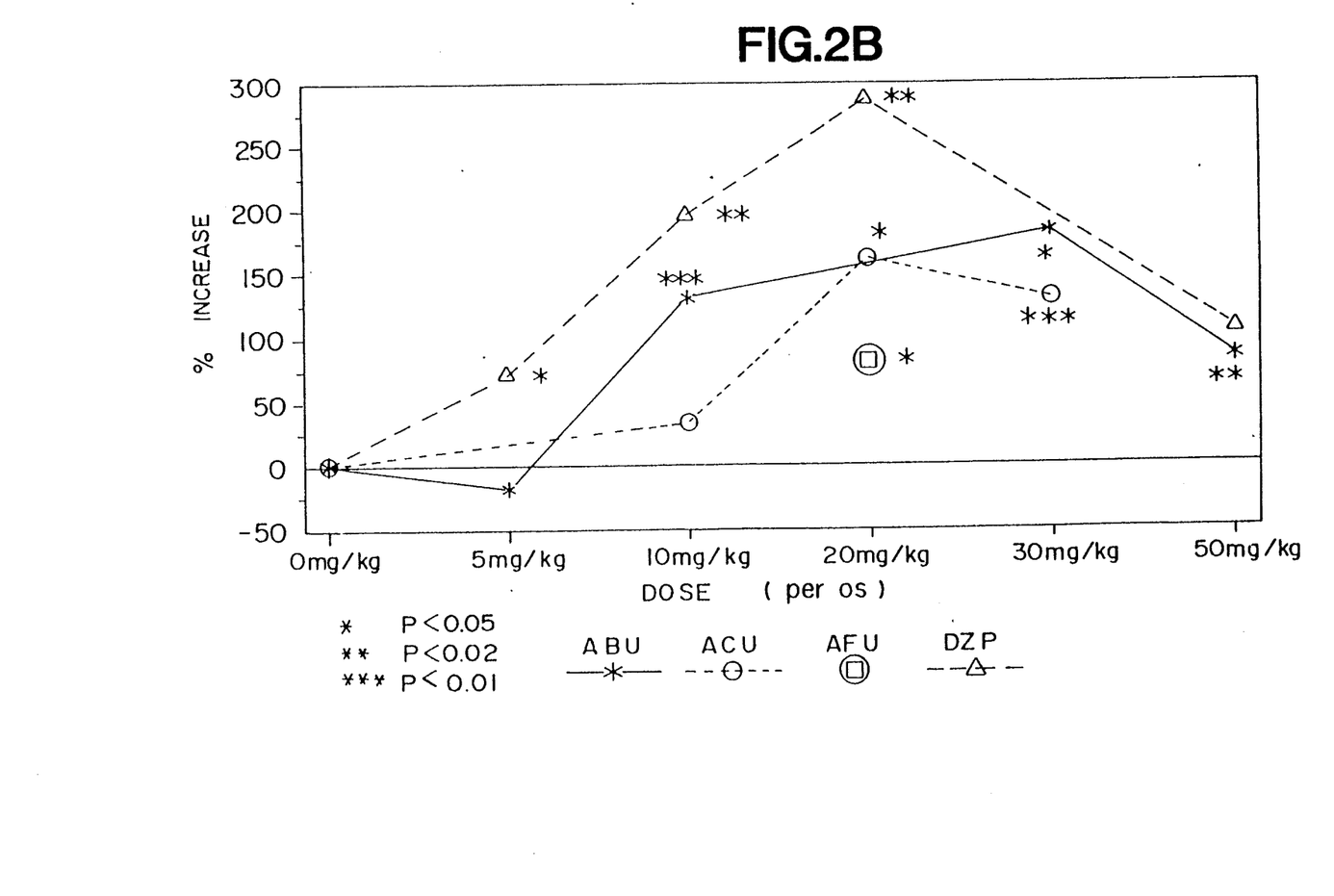
Figure 3:
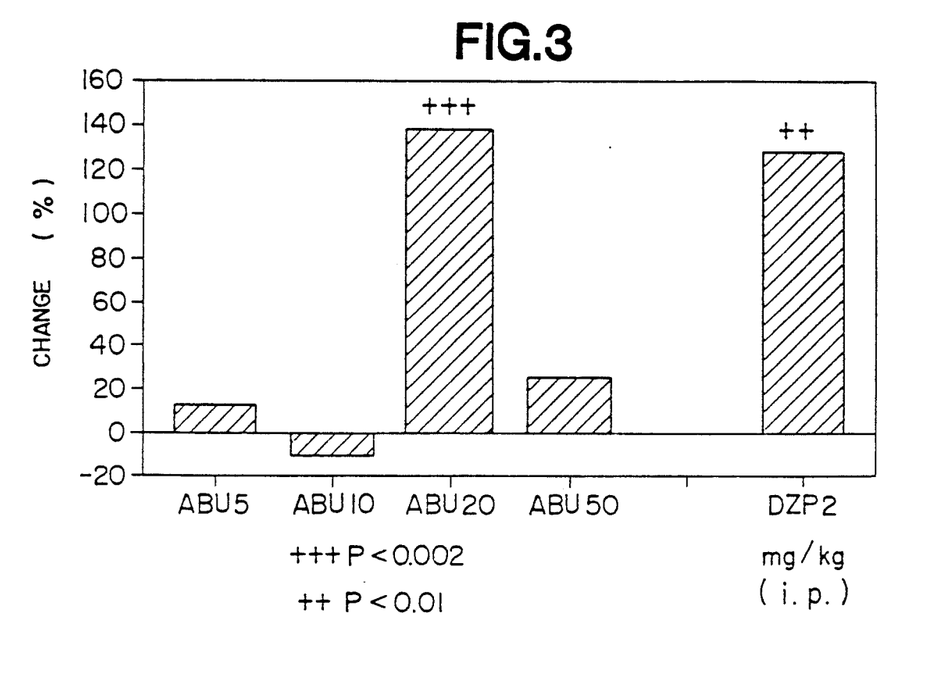
FIG. 3 is a graph showing the change (%) in the average number of water-drinking, obtained in Test Example 2 in which 1-amino-5-bromouracil was administered.

As is shown in FIG. 3, although the anti-conflict activity of the ABU was determined at the doses of 5, 10, 20 and 50 mg/kg, a significant increase in the number of water-drinking was noted only at the dose of 20 mg/kg.

On the other hand, the DZP significantly increased the number of water-drinking at the dose of 2 mg/kg. However, at the same dose, observations on the behaviors of the mice when they were receiving an electric shock (i.e., lack of both vocalization and escape behavior) revealed that the sensitivity of the mice to an electric shock was decreased. Therefore, such decrease is considered to have greatly contributed to the increase in the number of water-drinking.

However, no decrease in the sensitivity to an electric shock was noted when 20 mg/kg of the ABU was administered to the mice.

Test Example 3

Muscle Relaxant Activity

The muscle relaxant activities of the test compounds, 1-amino-5-bromouracil (ABU), 1-amino--5-chlorouracil (ACU) and diazepam (DZP), were determined in accordance with the method of L. L. Coughenour et al. [see Pharmacol. Biochem. & Behav., 6, 351-353 (1977)].

Male ICR mice were placed on a 13 cm×13 cm No. 4 wire screen, and the screen was then rotated by 180 degrees. Those mice which were able to return to the screen within one minute were referred to "successful" mice. The suspension of each test compound prepared in the same manner as in Test Example 1 was administered orally to the mice. The mice were then subjected to the above test. The dose of the test compound at which 50% of the mice successfully returned to the screen was determined as $ED_{50}$ (A). Only the mice which had been able to successfully return to the screen three times in succession before treatment with the test compound were used for the above test.

Further, the minimum effective dose (B) for anti-conflict activity of each of the above-described test compounds was determined on the basis of the results obtained in Test Example 1.

Furthermore, the validity of each of the test compounds as an anxiolytic drug was expressed as A/B value.

The results are shown in Table 1.

TABLE 1

| Test Compound | Muscle Relaxant Activity $ED_{50}$ (mg/kg) [A] | Minimum Effective Dose for Anti-Conflict Activity (mg/kg) [B] | Validity [A/B] |
| --- | --- | --- | --- |
| ABU | 74.1 | 10 | 7.4 |
| ACU | 46.0 | 20 | 2.3 |
| DZP | 8.8 | 5 | 1.8 |

Test Example 4

Acute Toxicity (intraperitoneal Administration)

1-Amino-5-bromouracil (ABU) was suspended in physiological saline containing 0.5% carboxymethyl cellulose (CMC). ABU was administered intraperitoneally to 8 ICR mice in a dose of 500 mg/kg, and their lethality was observed over a period of one week. As a result, all of the mice were found to be surviving and no death was observed.

Further, 1-amino-5-chlorouracil (ACU) was administered intraperitoneally to 10 male ICR mice in a dose of 357 mg/kg, and their lethality was observed over a period of one week. As a result, no death was observed.

Test Example 5

Acute Toxicity (Oral Administration)

The acute toxicity ($LD_{50}$ value) per oral administration was determined by the following method.

The test compound (1-amino-5-bromouracil (ABU) or 1-amino-5-chlorouracil (ACU) was suspended in distilled water containing 0.5% carboxymethyl cellulose (CMC). ABU or ACU was administered orally to male ICR mice (1 group: 10 mice) in a dose of 1000-2800 mg/kg or 500-1400 mg/kg, and the $LD_{50}$ values were determined according to the Litchfield-Wilcoxon method. The results are shown in Table 2.

TABLE 2

| Test Compound | $LD_{50}$ Value (mg/kg) | 95% Confidence Limit (mg/kg) |
| --- | --- | --- |
| ABU | 1923 | 1588-2330 |
| ACU | 971 | 791-1191 |

Preparation Example 1

| Tablet | |
| --- | --- |
| 1-Amino-5-bromouracil | 10 g |
| Corn starch | 65 g |
| Carboxymethylcellulose | 20 g |
| Polyvinylpyrrolidone | 3 g |
| Calcium stearate | 2 g |
| Total | 100 g |

Tablets each weighing 100 mg are prepared in a conventional manner. Each tablet contains 10 mg of 1-amino-5-bromouracil.

Preparation Example 2

| Powder and Capsule | |
| --- | --- |
| 1-Amino-5-fluorouracil | 20 g |
| Crystalline cellulose | 80 g |
| Total | 100 g |

Both the powders are mixed into a powder preparation. Separately, 100 mg of the preparation is charged into a No. 5 hard capsule to form a capsule preparation.

INDUSTRIAL APPLICABILITY

As is described above, 1-amino-5-halogenouracil represented by the previously-mentioned formula [I], which is an active ingredient of the anxiolytic drug of the present invention, has excellent anxiolytic activity while showing low muscle relaxant and sedative activities or like side effects, Which result in clinical problems, so that the compound is useful as an excellent anxiolytic drug. Moreover, the above compound has low toxicity, so that it can provide a therapeutic agent which is highly safe. Thus, the anxiolytic drug of the present invention can greatly contribute to a remedy for anxiety in mammal

What is claimed is:

1. A method of treating anxiety in mammal, which comprises administering an effective dose of a 1-amino-5-halogenouracil represented by the following formula (I):

wherein X represents a halogen atom, or a pharmaceutically acceptable salt thereof to a mammal in a state of anxiety.

2. A method according to claim 1 in which the 1-amino-5-halogenouracil is administered in a dosage of 50 mg per kg. of the mammal treated.

* * * * *